United States Patent [19]

Dean et al.

[11] Patent Number: 4,900,477

[45] Date of Patent: Feb. 13, 1990

[54] NOVEL INTERMEDIATES AND AN IMPROVED PROCESS FOR PRODUCING THE COMPOUND (3β,5α)-3-HYDROXYCHOLEST-8(14)-EN-15-ONE

[75] Inventors: William D. Dean, Congers, N.Y.; Robert F. R. Church, Cos Cob, Conn.; David N. Ridge, Upper Nyack, N.Y.

[73] Assignee: American Cyanamid Company, Stamford, Conn.

[21] Appl. No.: 174,273

[22] Filed: Mar. 28, 1988

[51] Int. Cl.$^4$ .................. C07J 0/00; A61K 31/56
[52] U.S. Cl. ...................... 260/397.4; 260/397.45; 260/397.5; 514/178; 514/179; 514/182
[58] Field of Search ............. 260/397.2, 397.3, 397.4, 260/397.5, 397.45; 514/177, 178, 182

[56] References Cited

U.S. PATENT DOCUMENTS 4,202,891 5/1980 Schroepfer, Jr. et al. ....... 260/397.2

OTHER PUBLICATIONS

Knight et al., J. Biol. Chem., 241, 1502–1508 (1966).
Martin et al., Biochem. & Biophys. Res. Comm., 39, 1170–1174 (1980).
Kamono et al., Can. J. Chem., 51, 1973–1976 (1973).
Parish et al., Chem. & Phys. of Lipids, 18, 233–239 (1977).
Parish et al., J. Org. Chem., 45, 4034–4037 (1980).
Dolle et al., J. Org. Chem., 51, 4047–4053 (1986).

*Primary Examiner*—Douglas W. Robinson
*Assistant Examiner*—Raymond J. Henley, III
*Attorney, Agent, or Firm*—Alan M. Gordon

[57] ABSTRACT

An improved process for the large scale production of the compound (3β,5α)-3-hydroxycholest-8(14)-en-15-one is described and two new compounds which have utility as intermediates in synthetic routes to the subject compound are disclosed.

17 Claims, No Drawings

NOVEL INTERMEDIATES AND AN IMPROVED PROCESS FOR PRODUCING THE COMPOUND (3β,5α)-3-HYDROXYCHOLEST-8(14)-EN-15-ONE

SUMMARY OF THE INVENTION

This invention is concerned with an improved process for the large scale production of the compound (3β,5α)-3-hydroxycholest-8(14)en-15-one.

The present invention also encompasses two new compounds that were discovered in our investigation of synthetic routes to the subject compound. Wherein both new compounds have utility as intermediates to prepare the subject compound, namely, the compounds: (3β,5α,7α,15α)-7-methoxy-cholest-8(14)ene-3,15-diol 3-benzoate and (3β,5o)-3-(benzoyloxy)cholest-7-en-15-one, said compounds will be described in greater detail hereinbelow.

BACKGROUND OF THE INVENTION

The compound (3β,5α)-3-hydroxycholest-8(14)-en-15-one is a known hypolipidemic agent (U.S. Pat. No. 4,202,891) which has the structure:

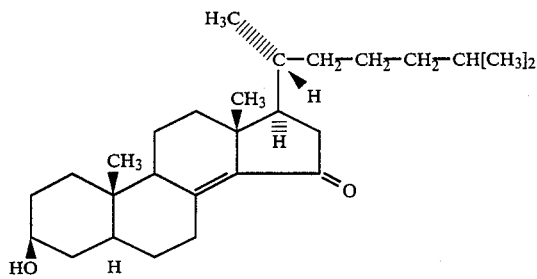

A method of preparing the subject compound from (3β,5α)-3-(benzoyloxy)cholest-8(14)en-15-one (prepared according to the technique of J. C. Knight et. al., *J. Biol. Chem.*, Vol. 241, p. 1502 (1966)) is disclosed in Example 1 of U.S. Pat. No. 4,202,891. The current procedure for the large scale production of (3β,5α)-3-hydroxycholest-8 (14)en-15-one essentially follows the stepwise synthetic route described hereinabove with the exception of the final step as shown in Scheme I.

Scheme I

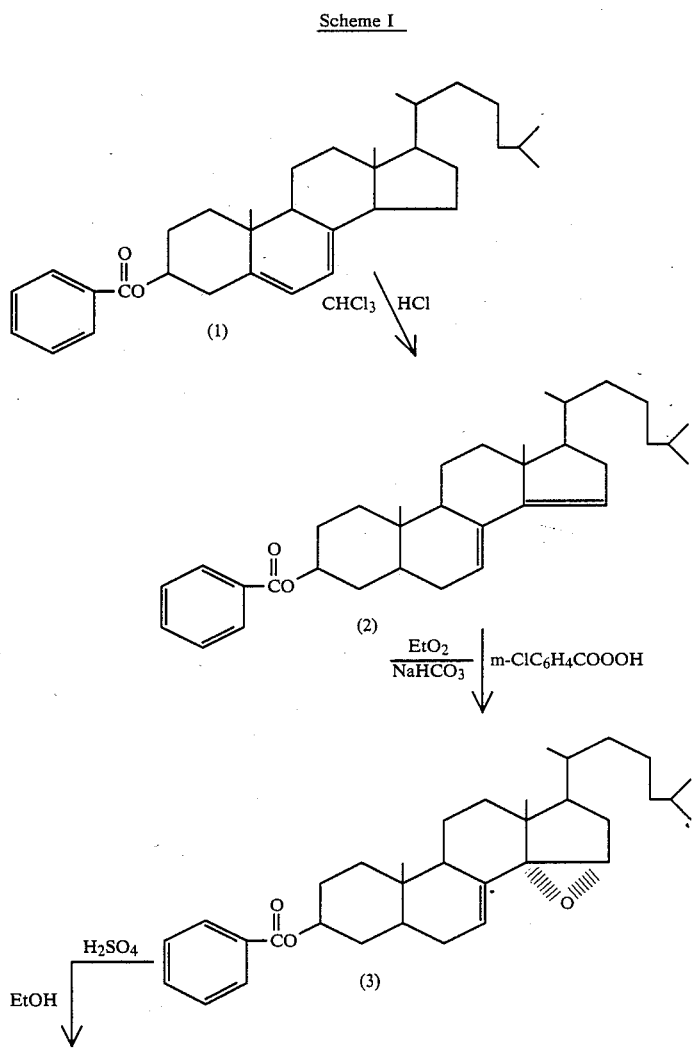

Scheme I

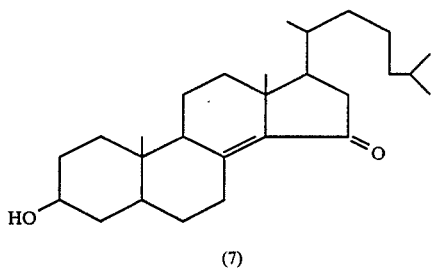

(7)

In accordance with Scheme I, isomerization of 5,7-cholestadien-3β-ol benzoate (I) with hydrogen chloride gas in chloroform gives the compound (3β,5α)-cholesta-7,14-dien-3-ol benzoate (2). Then epoxidation of (2) with m-chloroperbenzoic acid in diethyl ether in the presence of solid sodium bicarbonate in the cold gives the epoxide (3β,5α,15α)-14,15-epoxycholest-7-en-3-ol benzoate (3). The epoxide (3) is dissolved in ethanol and water. Then sulfuric acid is added, followed by heating at the reflux temperature for 24 hours to give the crude product (3β,5o)-3-hydroxycholest-8(14)en-15-one (7). The product (7) is recrystallized twice from methanol/heptane/water.

DESCRIPTION OF THE INVENTION

The present invention is concerned with a revised and improved process for the large scale production of (3β,5α)-3-hydroxycholest-8(14)en-15-one.

The invention also encompasses the discovery of two new intermediate compounds that have been isolated and identified in separate routes to the subject compound through the precursor compound (3β,5α)-3-(benzoyloxy)cholest-8(14)en-15-one, or to the subject compound directly.

This invention was derived from the known process diagramed in Scheme I. The step in Scheme I of isomeration of 5,7-cholestadien-3β-ol benzoate (1) to produce (3β,5α)cholesta-7,14-dien-3-ol benzoate (2) is also carried out in Scheme II and Scheme III. An acid such as hydrogen chloride, hydrogen bromide or concentrated sulfuric acid is used for the isomerization in a solvent such as chloroform, methylene chloride or other chlorinated or chlorofluoroalkanes such as carbon tetrachloride, 1,2-dichloroethane and $FCCl_3$. The use of hydrogen chloride in chloroform is preferred.

The novel variations which were made to the process of Scheme I are shown in the diagrams of Scheme II and Scheme III which follow hereinbelow. These changes resulted in improved productivity, added safety, technical convenience and time saving and provide a purer product.

Scheme II

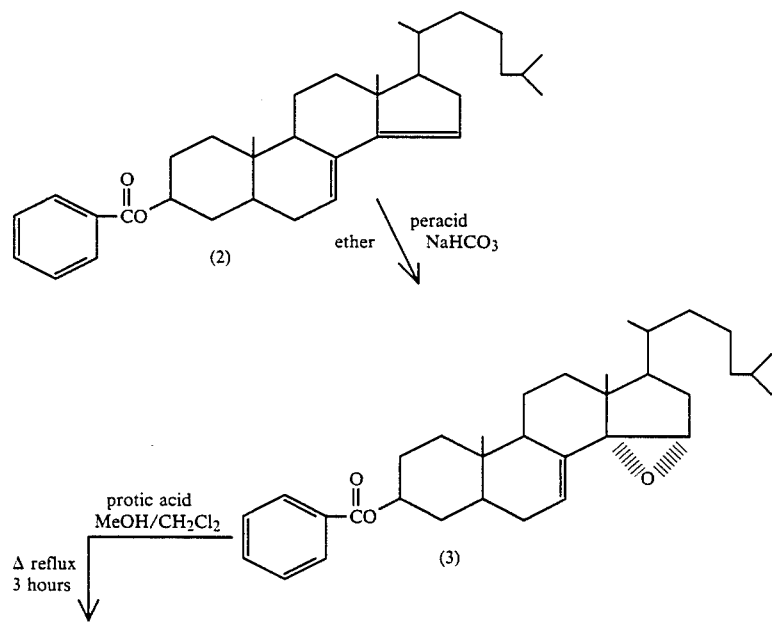

Scheme II -continued

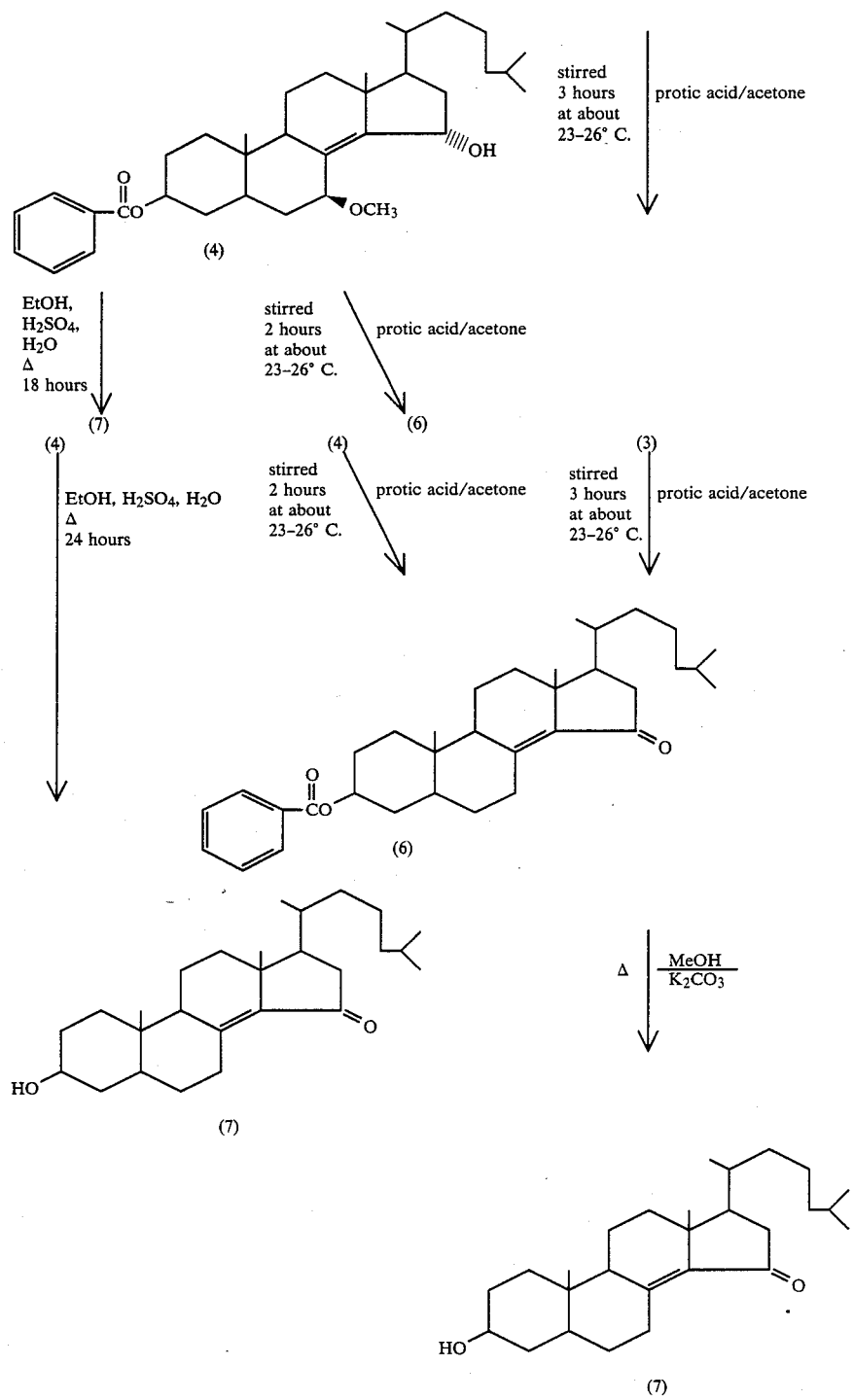

In accordance with Scheme II, the epoxidation of (3β,5α)cholesta-7,14-dien-3-ol benzoate (2) to (3β,5α,1-5α)-14,15-epoxycholest-7-en-3-ol benzoate (3) is carried out with a peracid at 0° C. to 20° C., using a suspension of the diene in t-butyl methyl ether instead of as a solution in diethyl ether (Scheme I). This change of solvent was made to promote greater productivity and safety. Examples of the peracids used include m-chloroperbenzoic acid, perbenzoic acid, peracetic acid and peroxybenzimidic acid The use of m-chloroperbenzoic acid is preferred. As alternatives to t-butyl methyl ether, one may use organic solvents such as tetrahydrofuran, dioxane, dimethoxyethane or ethyl acetate.

A modification of the procedure of G. R. Pettit and Y. Kamano, Can. J. Chem., 51 1973–1976 (1973) was applied to the next step as the epoxide (3) is stirred in acetone at 22° C. and is treated with a catalytic amount of aprotic acid at a temperature of about 23°-26° C. over a 3 hour period to provide the precursor compound (3β,5α)-3-(benzoyloxy)cholest-8(14)-en-15-one (6). Examples of such protic acids include perchloric acid, trifluoromethanesulfonic acid, methanesulfonic acid, trifluoroacetic acid and concentrated sulfuric acid. The use of 70% perchloric acid is preferred.

Then a stirred mixture of the precursor (6) in a protic solvent, preferably methanol, is treated with potassium carbonate and heated at reflux for 3 hours to give the desired product (3β,5α)-3-hydroxycholest-8(14)en-15-one (7). This conversion was based upon the procedures of E. J. Parish and G. J. Schroepfer and *J. Org. Chem.*, 45, 4034–4037 (1980) and R. E. Dolle and L. Kruse, *J. Org. Chem.*, 51, 4047–4053 (1986). Alternatively, the precursor (6) is treated with perchloric acid in n-propanol or ethanol at reflux or treated with potassium hydroxide or sodium hydroxide methanol at room temperature to give the desired product (7).

The two-step hydrolysis procedure described hereinabove is technically more convenient than the related art procedures in that a 24-hour refluxing period is avoided and the product obtained is cleaner, even without silica gel filtration.

Alternatively, as depicted in Scheme II, the epoxide (3) is added to 1:1 dichloromethane/methanol with a catalytic amount of a protic acid, preferably perchloric acid, and heated at reflux for 3–4 hours to give the novel intermediate compound (3β,5α7α,15α)-7-methoxycholest-8(14)ene-3,15-diol 3-benzoate (4).

Compound (4) does not show the characteristic streaking of the epoxide (3) by thin layer chromatography, using 10% ethyl acetate/hexane as the solvent system, on silica gel plates, but rather provides a discrete band at an Rf of about 0.1–0.2. The compound treated with a protic acid (preferably 70% perchloric acid) for 2 hours to obtain the precursor (3β,5α)-3-(benzoyloxy)cholest-8(14)en-15-one (6). The precursor (6) is dissolved in a protic solvent, preferably methanol, and treated with potassium carbonate as hereinbefore described to provide the desired product (7). The alternate procedures of Scheme II for the debenzoylation may also be used.

Alternatively, the intermediate (4) may be heated at reflux in a mixture of about 25/5/3 ethanol/sulfuric acid/water, respectively, for 24 hours as hereinbefore described to obtain the product (7).

Scheme III

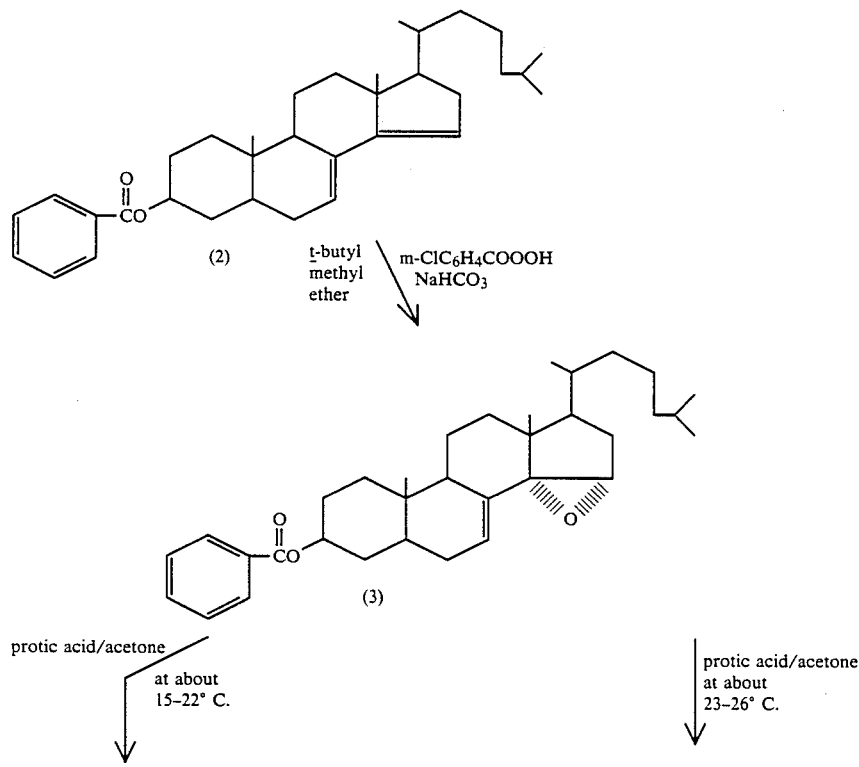

-continued

Scheme III

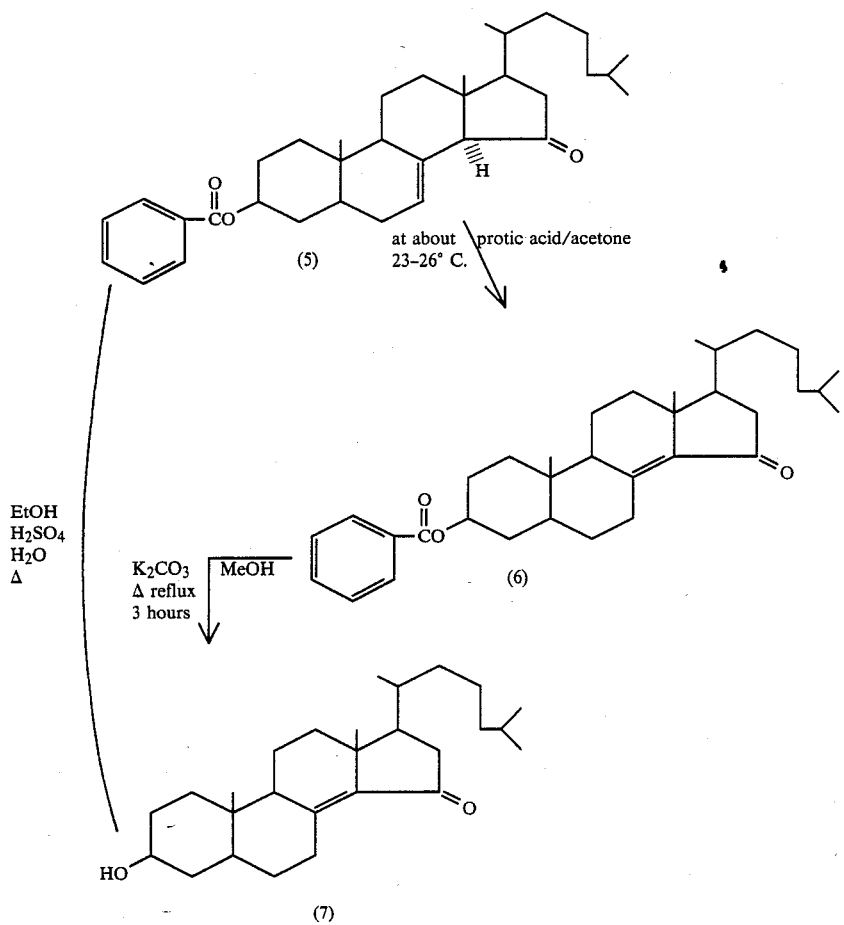

In accordance with Scheme III, the epoxidation of (3β,5α)cholesta-7,14-dien-3-ol benzoate (2) to (3β,5α, 15α)-14,15-epoxycholest-7-en-3-ol benzoate (3) is carried out as described in Scheme II. Also when the epoxyolefin (3) is treated with a catalytic amount of a protic acid (preferably 70% perchloric acid) in acetone at a controlled temperature of about 23°-26° C. for 3 hours, the precursor compound (3β,5α)-3-(benzoyloxy)cholest-8(14)en-15-one (6) is obtained. However, it has been discovered that when the preceding reaction is conducted at a temperature of from about 15°-22° C. for 3 hours, the novel intermediate compound (3β,5α)-3-(benzoyloxy)cholest-7-en-15-one (5) is produced Further treatment of (5) with a protic acid (preferably 70% perchloric acid) in acetone at about 23°-26° C. for 2 hours also gives the precursor compound (6) which is refluxed with potassium carbonate in a protic solvent, preferably methanol, as described hereinbefore in Scheme II to give the product (7). The alternate debenzoylation procedures described in Scheme II may also be used to give the product (7).

Alternatively, (5) may be hydrolyzed directly to the subject compound (7) by treatment with ethanol/ sulfuric acid/water at reflux.

This invention will be described in greater detail in conjunction with the following examples.

EXAMPLE 1

Preparation or (3β,5α)-cholesta-7 14-dien-3-ol benzoate (2)

A 2.4 kg amount of 5,7-cholestadien-3β-ol benzoate (1) was dissolved in 16 liters of chloroform in a 22-liter flask equipped with a low temperature thermometer, mechanical stirrer, nitrogen purge and gas inlet extending below the surface of the liquid. Nitrogen purge was started and the solution was agitated vigorously and cooled in dry ice-acetone to −65° C. Nitrogen purge was stopped and hydrogen chloride addition was started at a very slow rate (80 on a No. 2 flow meter, Gilmont Instruments, Inc.). The initially very exothermic reaction was stirred well, and hydrogen chloride addition was increased gradually, maintaining the temperature below −60° C. with dry ice-acetone. After one hour the flow meter was removed from the gas inlet line and the hydrogen chloride rate was regulated according to the reaction temperature (<−60° C.) Addition was continued until 1.6 kg of hydrogen chloride was introduced within two hours.

The wine-red solution was stirred at −60° C. to −65° C. for 30 minutes and drowned rapidly into a well-stirred mixture of 17 kg of ice and 10 liters of ammonium hydroxide at a temperature below −9° C. The mixture was stirred vigorously, the layers were allowed to separate and the chloroform layer (still <0° C.) was split and added to 900 ml of pyridine. The chloroform solution was washed twice with 14 liters of water, and evaporated at reduced pressure to a volume of about 5 liters. The thick crystalline mixture was diluted with stirring with 10 liters of acetone and allowed to stand overnight. The solid was filtered, washed with three 2-liter portions of acetone and air-dried to yield 1616 g (67%) of white crystals.

Analysis by 80 MHz 1-H nuclear magnetic resonance (NMR) determined that the product was a mixture of about 85-90% (3$\beta$,5$\alpha$)cholesta-7,14-dien-3-ol benzoate and 10-15% of the $\Delta^{8,14}$ diene.

EXAMPLE 2

Preparation of
(3$\beta$,5$\alpha$,15$\alpha$)-14,15-epoxycholest-7-en-3-ol benzoate (3)

A 24.55 kg amount of (3$\beta$,5$\alpha$)-cholesta-7,14-dien-3-ol benzoate (2) (prepared in the manner described in Example 1) and 6.41 g of sodium bicarbonate were suspended under nitrogen with good agitation in 240 liters of t-butyl methyl ether in a 200-gallon reactor and chilled to 0° C. A solution of 13.0 kg of m-chloroperbenzoic acid in 100 liters of t-butyl methyl ether at about 20° C. was added to the steroid-bicarbonate suspension over a 10 minute period. A mild exothermic reaction which raised the reaction mixture temperature to 10° C. was noted. The mixture was stirred for 2 hours then 150 liters of water were added. The mixture was stirred an additional hour and agitation was halted to allow separation of the phases. The lower aqueous layer was drained off and the remaining organic phase was treated with 50 liters of water, agitated vigorously, and then the aqueous portion was drained off. The product was filtered at about 10° C., washed with three 10 liter portions of methanol and air-dried to yield 19.1 k9 of (3) batch-A.

A second preparation was performed as described hereinabove using 24.0 kg of diene (prepared in the manner described in Example 1) with all other components being the same to yield 18.8 kg of product (3) batch-B.

The two batches of crude product A and B were combined and recrystallized as follows: The crude steroid (37.9 kg) was dissolved in 160 liters of toluene at 75° C. in a 200-gallon reactor. The mixture was cooled slowly to 45° C. and 320 liters of heptane was added. The mixture was chilled to 17° C. and filtered. The filter cake was washed with 20 liters of heptane, then dried to yield 28.4 kg of the product of the example (3) as white crystals (75% recovery).

EXAMPLE 3

Preparation of
(3$\beta$,5$\alpha$)-3-(benzoyloxy)cholest-8(14)-en-15-one (6)

A stirred mixture of 28.4 kg (3$\beta$,5$\alpha$,15$\alpha$)-14,15-epoxycholest-7-en-3-ol benzoate (3) (Example 2) in 280 liters of acetone, under nitrogen, in a 200gallon reactor, at 22° C. was treated with 100 ml of 70% perchloric acid. The mild exothermic reaction raised the reaction mixture temperature to 26° C. in about a 5 minute period The mixture was cooled to 21° C. and an additional 180 ml of 70% perchloric acid was added. The reaction mixture temperature was kept at 22±1° C. and the mixture was stirred for 3 hours to complete the reaction. The mixture was cooled and treated with 140 liters of water at 19° C. for 30 minutes, then stirred 20 minutes more. The solid was collected by filtration, washed with a large quantity of water and dried in vacuo at 40°-60° C. to give 29.3 kg of the desired crude product (6).

EXAMPLE 4

Preparation of
(3$\beta$,5$\alpha$)-3-hydroxycholest-8(14)en-15-one (7)

A stirred mixture of 29.3 kg of crude (3$\beta$,5$\alpha$)-3-(benzoyloxy)cholest-8(14)en-15-one (6) (Example 3) in 190 liters of methanol in a 100-gallon glass-lined reactor was treated with 8 5 kg of potassium carbonate, the mixture was heated to gentle reflux and held at reflux for 3 hours. The methanol solution was cooled, then was treated with 130 liters of water and 80 liters of heptane with vigorous stirring. The agitation was stopped and the mixture was chilled to 0° C. to −5° C. for 16 hours The crystalline mass was broken up by agitation and the solid was filtered, washed with 100 liters of methanol at 15° C, then air-dried to yield 21.3 kg of the desired crude product. The crude product was recrystallized as follows: A solution of the crude product, 21.3 kg, in 180 liters of methanol at about 45° C. was filtered through a pad of diatomaceous earth using nitrogen pressure. The filtrate was added to 200 liters of heptane at 45°-50° C. Then the solution was treated by vigorous agitation with 100 liters of water preheated to 60° C. The mixture was agitated for 10 minutes, then cooled to 35° C. over a 3-hour period, followed by standing at 25° C. for 24 hours and finally the mixture was chilled to 3° C.

The crystalline mass which formed was broken up by vigorous agitation and filtered. The solid was washed with about 180 liters of water, 20 liters of methanol and 20 liters of heptane, then was dried in Vacuo at 40° C. to constant weight to yield 15.3 kg of the product of the example (7).

EXAMPLE 5

Preparation of
(3$\beta$,5$\alpha$,7$\alpha$,15$\alpha$)-7-methoxycholest-8(14)ene-3,15-diol 3-benzoate (4)

A mixture of 25.0 g of (3$\beta$,5$\alpha$,15$\alpha$)-14,15-epoxycholest-7-en-3-ol benzoate (3) (Example 2), 200 ml of methanol, 200 ml of dichloromethane and one drop of perchloric acid was heated at the reflux temperature for 3 hours, then the mixture was cooled and evaporated in vacuo to give a white solid. The solid was recrystallized from hexane to give 20.0 g of the product of the example (4), mp 182°-183° C.

EXAMPLE 6

Preparation of
(3$\beta$,5$\alpha$)-3-(benzoyloxy)cholest-8(14)en-15-one (6) from (3$\beta$,5$\alpha$,7$\alpha$,15$\alpha$)-7-methoxycholest-8(14)-ene-3.15-diol 3-benzoate (4)

A 5.0 g amount of (3$\beta$,5$\alpha$,7$\alpha$,15$\alpha$)-7-methoxycholest-8(14)ene-3,15-diol 3-benzoate (4) (Example 5) was suspended and stirred in 50 ml of acetone at room temperature, then 3 drops of 70% perchloric acid were added and after 10 minutes a clear solution resulted. Stirring was continued and after 30 minutes a solid began to deposit. After stirring for 2 hours, 25 ml of water was added to the mixture and the solid was collected by filtration to give 4.7 g of the desired product, which was authenticated by 300 MHz 1-H NMR.

EXAMPLE 7

Comparative preparation of
(3β,5α)-3-(benzoyloxy)-cholest-8(14)en-15-one (6)
from(3β,5α,15α)-14,15-epoxycholest-7-en-3-ol
benzoate (3)

A 5.0 g amount of (3β,5α,15α)-14,15-epoxycholest-7-en-3-ol benzoate (3) (Example 2) was suspended and stirred in 50 ml of acetone and the procedure of Example 6 was followed throughout to obtain 4.8 g of the desired product.

EXAMPLE 8

Preparation of (3β,
5=)-3-hydroxycholest-8(14)en-15one (7) by the
hydrolysis of (3β,5α,
7α,15α)-7-methoxycholest-8(14)ene-3,15-diol
3-benzoate (4)

A 1.2 g portion of (3β,5α,7α,15α)-7-methoxycholest-8(14)ene-3,15-diol 3-benzoate (4), (prepared as described in Example 5) was suspended in 30 ml of 95% ethanol and 3.5 ml of water and cooled to 5°–10° C. in an ice bath. Then 6.5 ml of concentrated sulfuric acid was cautiously added with stirring. The resulting mixture was heated at reflux for about 18 hours, then the dark solution was cooled to room temperature and poured into an ice-water mixture. The resulting gummy solid was collected by filtration then purified by crystallization from the methanol/heptane/water system described in Example 4 to obtain the desired product (7).

EXAMPLE 9

Preparation of
(3β,5α)-3-(benzoyloxy)-cholest-7-en-15-one (5)

A 50 gallon glass lined reactor was charged with 100 liters of acetone and 10.0 kg of (3β,5α,15α)-14,15-epoxycholest-7-en-3-ol benzoate (3) (prepared as described in Example 2) were added at 22° C. over a 10 minute period. The reaction mixture was chilled with water for 45 minutes to a temperature of 13° C., then 100 ml of 70% perchloric acid were added in 20 ml portions over 15 minutes with a temperature rise to 15° C. The reaction mixture was stirred for 2 hours and 50 minutes while the temperature was maintained at or below 22° C.

Then, 50 liters of water were added to the reaction mixture in 5 liter portions over 20 minutes at a temperature of 22°–25° C. The mixture was stirred for 30 minutes and the solid was collected by rapid filtration. The reaction vessel and cake were washed twice with 20 liters of water to give 26.35 kg of crude product on an "as is" basis A 13.2 kg amount of this material was washed with 2–3 liters of water, and was sucked dry with vacuum for 3 hours. The cake was dried in vacuo at room temperature for about 60 hours to give 4.48 kg of dried product (5).

EXAMPLE 10

Preparation of
(3β,5α)-3-(benzoyloxy)-cholest-7-en-15-one (5)

The procedure of Example 9 was followed as a 200 gallon glass lined reactor vessel was charged with 260 liters of acetone at 24° C., followed by the addition of 26.00 kg of (3β,5α,15α)-14,15-epoxycholest-7-en-3-ol benzoate (3) at 23° C. The mixture was chilled with water at 18° C and stirred for 10 minutes and 260 ml of 70% perchloric acid was added in four-50 ml portions and one 60 ml portion over 30 minutes at temperatures for 20° C. to 22° C. The reaction mixture was stirred for 3 hours, decreasing the temperature from 20° C. to 15° C. Thin layer chromatography (TLC) on silica gel plates using 10% ethyl acetate in hexanes as the solvent system indicated no change in product composition during the last hour of reaction. Then 130 liters of water were added to the reaction mixture in 5 liter portions over a 15 minute period at a temperature of 14° C. to 16° C. and the reaction mixture was stirred for one hour and forty minutes. The solid was collected by rapid filtration and washed with 20 liter and 40 liter portions of water, sucked dry with vacuum, and air-dried for several days to give 37.55 kg of product on an "as is" basis. An 18.8 kg amount of the "as is" product was dried in vacuo at room temperature for about 60 hours to give 12.28 kg of dried product, similar to the product of Example 9 by TLC.

EXAMPLE 11

Preparation of (3β,5
α)-3-(benzoyloxy)cholest-8(14)en-15-one (6) from
(3β,5α)-3-(benzoyloxy)-cholest-7-en-15-one (5)

A 100 gallon glass lined reactor was flushed with nitrogen gas for 10 minutes and 161 liters of acetone were added over a 15-minute period at a temperature of 23° C., under a slight vacuum. While still under nitrogen, 16.08 kg of (3β,5α)-3-(benzoyloxy)-cholest-7-en-15-one (5) (prepared as described in Examples 9 and 10) were added to the reaction vessel. The reaction mixture was cooled to 22° C. and 161 ml of 70% perchloric acid was added at one, 7 and 12 minutes in 40, 70 and 51 ml portions, respectively, at reaction mixture temperatures of 22° C., 21° C. and 21° C., respectively. Stirring was continued for 3 hours at 21° C. to 18° C. Then a total of 120 liters of water and 40 kg of ice was added portionwise over 45 minutes, providing a reaction mixture temperature of about 12° C. The solid was collected and washed with three-20 liter portions of water, then dried in vacuo at 24° C. for 16 hours to give 21.17 kg of the desired product (6) on an "as is" basis.

EXAMPLE 12

Preparation of
(3β,5α)-3-hydroxycholest-8(14)-en-15-one (7) from
(3β,5α)-3-(benzoyloxy)cholest-8-(14)en-15-one (6)

A 100 gallon glass-lined reactor vessel was flushed with nitrogen gas for about 15 minutes. Then 96.0 liters of methanol was added, followed by 21.17 kg of crude (3β,5α)-3-(benzoyloxy)cholest-8(14)en-15-one (6). (Example 11) and 4.8 kg of anhydrous potassium carbonate. The reaction mixture was heated to reflux and maintained at reflux for 3 hours. Water cooling of the reactor was started and 96 liters of n-heptane were added followed by 43 liters of water. The mixture was stirred vigorously for a few minutes then agitation was stopped. The mixture was seeded with iodine crystals, then cooled to <10° C. for 16 hours. The mixture was stirred vigorously for 10–15 minutes and the solid was collected by filtration, washed with 12 liters of cold methanol (−5° C.), then 12 liters of cold n-heptane (−5° C.). The material was dried in vacuo at room temperature for 16 hours to give 9.7 kg of the desired crude product (7).

EXAMPLE 13

Preparation of
(3β,5α)-3-hydroxycholest-8(14)en-15-one (7) by the hydrolysis of
(3β5α)-3-(benzoyloxy)-cholest-7-en-15-one (5)

A 1.2 g portion of (3β,5α)-3-(benzoyloxy)-cholest-7-en-14-one (5) prepared as described in Example 9 was refluxed in a mixture of 30 ml of ethanol, 3.5 ml of water and 6.5 ml of sulfuric acid as described in Example 8. The work-up and crystallization procedure of Example 8 was followed to obtain the desired product (7).

We claim:

1. The compound (3β,5α,7α,15α)-7-methoxycholest-8(14)ene-3,15-diol 3-benzoate.

2. The compound (3β,5α) 3-(benzoyloxy) cholest-7-en-15-one.

3. A process for producing (3β,5α)-3-hydroxycholest-8(14)en-15-one, which comprises the steps of:
   (a) dissolving 5,7-cholestadien-3β-ol benzoate in chloroform, purging with nitrogen as the solution is e cooled to −65° C. in dry ice-acetone, adding an acid for an effective time while maintaining the below −60° C., then treating the solution with ice and ammonium hydroxide, separating the chloroform layer and adding it to pyridine, washing the chloroform layer with water, collecting the compound (3β,5α) cholesta-7,14-dien-3-ol benzoate by filtration, which is then washed with water and dried, then
   (b) treating a suspension of (3β,5α)cholesta-7,14-dien-3-ol benzoate and sodium bicarbonate in t-butyl methyl ether with a solution of a peracid in an organic solvent at 0° C. to 20° C. for an effective time, then treating the organic mixture with water and collecting the compound (3β,5α,15α)-14,15-epoxycholest-7-en-3-ol benzoate by filtration at about 10° C., washing the solid with an effective amount of methanol and recrystallizing the crude product from toluene:heptane (1:2) at an effective temperature, then
   (c) the recrystallized epoxide is stirred in acetone at 22° C. to 26°0 C., under nitrogen, and is treated with a catalytic amount of a protic acid for an effective time, then the mixture is treated with excess water at about 19° C. for an effective time and the crude product (3β,5α)-3-(benzoyloxy)cholest-8(14)en-15-one is collected by filtration, washed with water and dried in vacuo, then
   (d) a stirred mixture of the preceding crude product is treated for an effective time with (1) potassium carbonate in a protic solvent and heated at reflux, or (2) perchloric acid in n-propanol or ethanol at reflux, or (3) potassium hydroxide or sodium hydroxide in methanol at room temperature to give the desired product (3β,5α)-3-hydroxycholest-8(14)en-15-one which is recrystallized from methanol, water and heptane at an effective chilling temperature for an effective time and is collected by filtration and washed with methanol.

4. The process of claim 3 wherein the acid of step (a) is hydrogen chloride, hydrogen bromide or sulfuric acid, the peracid of step (b) is m-chloroperbenzoic acid, perbenzoic acid, peracetic acid or peroxybenzimidic acid, the organic solvent of step is t-butyl methyl ether tetrahydrofuran, dioxane dimethoxyethane or ethyl acetate, the protic acid of step (c) is perchloric, trifluoromethanesulfonic, methanesulfonic, trifluoroacetic or sulfuric, and the protic solvent of step (d)(1) is methanol.

5. The process of claim 4 wherein the acid of step (a) is hydrogen chloride, the peracid of step (b) is m-chloroperbenozic acid, the organic solvent of step (b) is t-butyl methyl ether, the protic acid of step (c) is perchloric acid and the product of step (c) is treated with potassium carbonate in methanol and heated at reflux.

6. A process for producing (3β,5α)-3-hydroxy-cholest-8(14)en-15-one which comprises:
   (a) dissolving 5,7-cholestadien-3β-ol benzoate in chloroform, purging with nitrogen as the solution is cooled to −65° C. in dry ice-acetone, adding an acid for an effective time while maintaining the temperature below −60° C., then treating the solution with ice and ammonium hydroxide. separating the chloroform layer and adding it to pyridine, washing the chloroform layer with water, collecting the compound (3β,5α) cholesta-7,14-dien-3-ol benzoate by filtration, which is then washed with water and dried, then
   (b) treating a suspension of (3β,5α)cholesta-7,14-dien-3-ol benzoate and sodium bicarbonate in t-butyl methyl ether with a solution of a peracid in an organic solvent at 0° to 20° C. for an effective time, then treating the organic mixture with water and collecting the compound (3β,5α,15α)-14,15-epoxycholest-7-en-3-ol benzoate by filtration at about 10° C., washing the solid with an effective amount of methanol and recrystallizing the crude product from toluene:heptane (1:2) at an effective temperature, then
   (c) adding the recrystallized epoxide to 1:1 dichloromethane:methanol containing a catalytic amount of a protic acid and heating the mixture at the reflux temperature for an effective time then cooling the mixture and evaporating the solvents in vacuo to obtain the novel intermediate compound (3β,5α,7α,15α)-7-methoxycholest-8 (14)ene-3,15-diol 3-benzoate, and recrystallizing the product from hexane, then
   (d) stirring the preceding novel intermediate compound in acetone at about 23°–26° C. and treating the solution with a catalytic amount of a protic acid for 2 hours to obtain the crude product (3β,5α)-3-(benzoyloxy)-cholest-8 (14)en-15-one, which is then treated as described in claim 3(d) to obtain the subject compound (3β,5α)-3-hydroxycholest-8(14)en-15-one; and
   (e) alternatively, heating a suspension of the novel intermediate compound of step (a) above in a mixture of ethanol, sulfuric acid and water at the reflux temperature for an effective time, then recrystallizing the subject compound (3β,5α)-3-hydroxycholest8(14)en-15-one from methanol, heptane and water at an effective temperature in an effective time.

7. The process of claim 6 wherein the protic acid of step (c) is perchloric acid, the protic acid of step (d) is perchloric, trifluoromethanesulfonic, methanesulfonic, trifluoroacetic or sulfuric.

8. The process of claim 7 wherein the protic acid of step (d) is perchloric acid.

9. A process for producing (3β,5α)-3-hydroxycholest-8(14)en-15-one, which comprises:
   (a) dissolving 5,7-cholestadien-3βol benzoate in chloroform, purging with nitrogen as the solution is cooled to −65° C. in dry ice-acetone adding an acid for an effective time while maintaining the temperature below −60° C., then treating the solution with ice and ammonium hydroxide, separating the chloroform layer and adding it to pyridine, washing the chloroform layer with water, collecting the compound (3β,5α)cholesta-7,14-dien-3-ol benzoate by filtration, which is then washed with water and dried, then (b) treating a suspension of (3β,5α)cholesta-7,14-dien-3-ol benzoate and sodium bicarbonate in t-butyl methyl ether with a solution of a peracid in an organic solvent at 0° to 20° C. for an effective time, then treating the organic mixture with water and collecting the compound (3β,5α,15α)-14,15-epoxycholest-7-en-3-ol benzoate by filtration at about 10° C., washing the solid with an effective amount of methanol and recrystallizing the crude product from toluene:heptane (1:2) at an effective temperature, then (c) treating the epoxide (3β,5α,15α)-14,15-epoxycholest-7-en-3-ol benzoate with a catalytic amount of a protic acid in acetone at a controlled temperature of about 15° C. to about 22° C. for 3 hours to the novel intermediate compound (3β,5α)-3-(benzoyloxy)-cholest-7-en-15-one, then (d) further treating the preceding compound with a catalytic amount of a protic acid in acetone at about 23°-26° C. for 2 hours to give the precursor compound (3β,5α)-3-(benzoyloxy)cholest-8(14)en-15-one which is then treated for an effective time with (1) potassium carbonate in a protic solvent and heated at reflux, or (2) perchloric acid in n-propanol or ethanol at reflux, or (3) potassium hydroxide or sodium hydroxide in methanol at room temperature to provide the subject compound (3β,5α)-3-hydroxycholest-8(14)en-15-one which is recrystallized from methanol, water and heptane at an effective chilling temperature for an effective time and is collected by filtration and washed with methanol; or (e) alternatively, heating a suspension of the novel intermediate compound of step (c), (3β,5α)-3-(benzoyloxy) cholest-7-en-15-one in a mixture of ethanol, sulfuric acid and water at the reflux temperature for an effective time, then recrystallizing the subject compound (3β,5α)-3-hydroxycholest-8(14)en-15-one from methanol, heptane and water at an effective temperature for an effective time.

10. The process of claim 9 wherein the protic acid of steps (c) and (d) is perchloric, trifluoromethanesulfonic, methanesulfonic, trifluoroacetic or sulfuric.

11. The process of claim 10 wherein the protic acid of steps (c) and (d) is perchloric.

12. A process for producing (3β,5α,7α,15α)-7-methoxycholest-8(14)ene-3, 15-diol 3-benzoate which comprises the steps of:

(a) dissolving 5,7-cholestadien-3β-ol benzoate in chloroform, purging with nitrogen as the solution is cooled to −65° C. in dry ice-acetone, adding an acid for an effective time while maintaining the temperature below −60° C., then treating the solution with ice and ammonium hydroxide, separating the chloroform layer and adding it to pyridine, washing the chloroform layer with water, and collecting the compound (3β,5α)-cholesta-7,14-dien-3-ol benzoate by filtration, which is then washed with water and dried, then (b) treating a suspension of (3β,5α)cholesta-7,14-dien-3-ol benzoate and sodium bicarbonate in t-butyl methyl ether with a solution of a peracid in an organic solvent at 0° C. for an effective time, then treating the organic mixture with water and collecting the compound (3β,b 5α,15α)-14,15-epoxycholest-7-en-3-ol benzoate by filtration at about 10° C., washing the solid with an effective amount of methanol and recrystallizing the crude product from toluene:heptane (1:2) at an effective temperature, then (c) adding the epoxide to 1:1 dichloromethane: methanol containing a catalytic amount of a protic acid and heating the mixture at the reflux temperature for an effective time, then cooling the mixture and evaporating the solvents in vacuo to obtain the novel intermediate compound (3β,5α,7α,15α)-7-methoxy-cholest8(14)ene-3,15-diol 3-benzoate, and recrystallizing the product from hexane.

13. The process of claim 12 wherein the acid of step (a) is hydrogen chloride, hydrogen bromide or sulfuric acid, the peracid of step (b) is m-chloroperbenzoic acid, perbenzoic acid, peracetic acid or peroxybenzimidic acid, the organic solvent of step (b) is t-butyl methyl ether, tetrahydrofuran, dioxane, dimethoxyethane or ethyl acetate, and the protic acid of step (c) is perchloric, trifluoromethanesulfonic, methanesulfonic, trifluoroacetic or sulfuric.

14. The process of claim 13 wherein the acid of step (a) is hydrogen chloride, the peracid of step (b) is m-chloroperbenzoic acid, the organic solvent of step (b) is t-butyl methyl ether and the protic acid of step (c) is perchloric acid.

15. A process for producing (3β,5α)-3(benzoyloxy) cholest-7-en-15-one which comprises the steps of:

(a) dissolving 5,7-cholestadien-3β-ol benzoate in chloroform, purging with nitrogen as the solution is cooled to −65° C. in dry ice-acetone, adding an acid for an effective time while maintaining the temperature below −60° C., then treating the solution with ice and ammonium hydroxide, separating the chloroform layer and adding it to pyridine, washing the chloroform layer with water, and collecting the compound (3β,5α)cholesta-7,14-dien-3-ol benzoate by filtration, which is then washed with water and dried, then (b) treating a suspension of (3β,5α)cholesta-7,14-dien-3-ol benzoate and sodium bicarbonate in t-butyl methyl ether with a solution of a peracid in an organic solvent at 0° C. to 20° C. for an effective time, then treating the organic mixture with water and collecting the compound (3β,5α,15α)-14,15-epoxycholest-7-en-3-ol benzoate by filtration at about 10° C., washing the solid with an effective amount of methanol and recrystallizing the crude product from toluene:heptane (1:2) at an effective temperature, then (c) treating the epoxide with a catalytic amount of a protic acid in acetone at a controlled temperature of about 15° C. to about 22° C. for 3 hours to give the novel intermediate compound (3β,5α)-3-(benzoyloxy)cholest-7-en-15-one.

16. The process of claim 15 wherein the acid of step (a) is hydrogen chloride, hydrogen bromide or sulfuric acid, the peracid of step (b) is m-chloroperbenzoic acid, perbenzoic acid, peracetic acid or peroxybenzimidic acid, the organic solvent of step (b) is t-butyl methyl ether, tetrahydrofuran, dioxane, dimethoxyethane or ethyl acetate, the protic acid of step (c) is perchloric, trifluoromethanesulfonic, methanesulfonic, trifluoroacetic or sulfuric.

17. The process of claim 16 wherein the acid of step (a) is hydrogen chloride, the peracid of step (b) is m-chloroperbenzoic acid, the organic solvent of step (b) is t-butyl methyl ether and the protic acid of step (c) is perchloric acid.

* * * * *